(12) United States Patent
Deng (10) Patent No.: US 11,369,738 B2
(45) Date of Patent: Jun. 28, 2022

(54) DRIP DEVICE

(71) Applicant: Shenzhen Bona Pharma Technology Co., Ltd., Guangdong (CN)

(72) Inventor: Yunhua Deng, Shenzhen (CN)

(73) Assignee: Shenzhen Bona Pharmea Techology Co., Ltd., Guangdong (CN)

( * ) Notice: Subject to any disclaimer, the term of this patent is extended or adjusted under 35 U.S.C. 154(b) by 33 days.

(21) Appl. No.: 16/639,562

(22) PCT Filed: Aug. 10, 2018

(86) PCT No.: PCT/CN2018/099937
§ 371 (c)(1),
(2) Date: Feb. 15, 2020

(87) PCT Pub. No.: WO2019/033997
PCT Pub. Date: Feb. 21, 2019

(65) Prior Publication Data
US 2020/0222629 A1    Jul. 16, 2020

(30) Foreign Application Priority Data

Aug. 16, 2017 (CN) .......................... 201710703195.X (51) Int. Cl.
*A61M 5/168* (2006.01)
*A61M 5/14* (2006.01)

(52) U.S. Cl.
CPC ...... *A61M 5/16813* (2013.01); *A61M 5/1411* (2013.01)

(58) Field of Classification Search
CPC ...... A01G 25/023; A61M 2005/14506; A61M 31/00; A61M 5/1411; A61M 5/145; A61M 5/1452; A61M 5/1454; A61M 5/168; A61M 5/16809; A61M 5/16813; A61M 5/1689; B01L 3/0272; B05B 1/02; B05B 11/0059; B05B 11/0062; B05B 11/0064; B05B 11/0067; B05B 11/0072; B05B 11/30; B05B 11/3001; B05B 11/3004; B05B 11/3016; B05B 11/3021; B05B 11/3022; B05B 11/3038; B05B 11/304;
(Continued)

(56) References Cited

U.S. PATENT DOCUMENTS

| | | | |
|---|---|---|---|
| 5,176,296 A * | 1/1993 | Lina .................... | B05B 11/3018 137/854 |
| 9,095,864 B2 * | 8/2015 | Petit ..................... | B05B 1/3436 |

(Continued)

*Primary Examiner* — Shefali D Patel (57) ABSTRACT

The present disclosure relates to a drip device, including a drip bottle having a bottle mouth facing downward, since the bottle mouth faces downward, a liquid in the drip bottle is charged into a first connecting tube, an infusion channel, and a piston chamber when a pressing head is not pushed upward, a plug blocks a drip port, and the liquid cannot flow out from the drip port. When the pressing head is pushed upward to move the pressing head upward relative to a connecting cover, a piston head inserts into a piston chamber to separate the infusion channel from the piston chamber, the pressing head continues to move upward, a volume of the piston chamber is compressed, the liquid in the piston chamber will flow back to the drip bottle through a liquid outlet, and a volume of the infusion channel is also compressed.

9 Claims, 8 Drawing Sheets

(58) Field of Classification Search
CPC ..... B05B 11/3073; B05B 11/309; B65D 1/08; B65D 47/18
See application file for complete search history.

(56) References Cited

U.S. PATENT DOCUMENTS

2009/0028734 A1    1/2009  Tseng
2014/0070030 A1*  3/2014  Harms ................ A61J 1/1475
                                                239/583

* cited by examiner

FIG. 1

View A

View B

FIG. 4

View C

DRIP DEVICE

CROSS REFERENCE TO RELATED APPLICATION

This is a Sect. 371 National Stage of PCT International Application No. PCT/CN2018/099937, filed on 10 Aug. 2018, which claims priority of a Chinese Patent Application No. 201710703195X filed on 16 Aug. 2017, the contents of both applications hereby being incorporated by reference in their entireties for all purposes.

BACKGROUND

Field of Disclosure

The present disclosure relates to a drip device, in particular, to a drip device for quantitatively extruding a liquid in the field of medical technology.

Description of Related Arts

Drip devices are widely used in various industries, techniques, medicine, food and other fields. Fluid product dispensing pumps are well known and are commonly used in the field of pharmaceuticals to dispense liquid formulations. Fluid product dispensing pumps typically have a pump body, a piston slides in the pump body to dispense a dose of fluid product each time it is actuated. Especially for pharmaceutical products, the pump sometimes includes a plug that is placed at a dispensing orifice. These plugs are used in particular to avoid contamination of the fluid product between two actuations of the pump and are therefore urged to their occlusion position when they are stopped. The plugs may be accompanied by a variety of problems. Therefore, the seal is typically implemented at the end of any return stroke, and thus has a time slot when contamination may occur between the end of dispensing of the fluid product agent and the effective closure of the dispensing orifice.

Similarly, when actuated, the seal is usually lost from the beginning of any actuation stroke, and product dispensing often occurs only at the end of the actuation stroke. The time slot is still sufficient to cause contamination. Moreover, in the closed position, to ensure sealing, the plug is actuated by a spring, thus the plug exerts a force on a dispensing head portion that mates with the plug, typically on a peripheral edge portion of the dispensing orifice. However, especially for nasal spray heads, and in particular for pediatric spray heads, the dispensing orifice walls are very thin, the thrust exerted by the plugs can cause deformation of the spray head, thus leading to a loss of sealing and a risk of contamination in consequence.

SUMMARY OF THE PRESENT DISCLOSURE

The present disclosure provides a drip device, which can reduce the risk of external foreign matter contaminating a liquid agent.

The present disclosure provides a drip device, including a drip bottle having a bottle mouth facing downward, the bottle mouth is connected with a connecting cover, a lower end of the connecting cover is connected with a pressing head, the pressing head is reciprocally movable up and down with respect to the connecting cover; a first connecting tube extending downward is placed at the lower end of the connecting cover, a drip port is placed at a lower end of the pressing head, a second connecting tube is placed upward from the drip port, an upper end of the second connecting tube extends into the first connecting tube and is slidably sealed with an inner side wall of the first connecting tube.

A piston head extending downward is placed in the first connecting tube, a connecting rod is placed in the second connecting tube, a connecting block is placed at an upper end of the connecting rod, the connecting block contains a piston chamber having an opening facing upward, a plug is placed at a lower end of the connecting rod, and the plug blocks the drip port; an infusion channel is formed by the inner side wall of the first connecting tube, an inner side wall of the second connecting tube, an outer side wall of the piston head, an outer side wall of the connecting block, and an outer side wall of the connecting rod; a liquid outlet communicating with the bottle mouth is placed at a lower end of the piston head, the infusion channel communicates with the liquid outlet through the piston chamber.

When the pressing head moves upward relative to the connecting cover, the piston head inserts into the piston chamber to separate the infusion channel from the piston chamber, so that the liquid pressure in the infusion channel increases and the connecting rod is lifted up, thus the plug is moved upward to open the drip port.

Preferably, when the piston head inserts into the piston chamber, the outer side wall of the piston head is slidably sealed with an inner side wall of the piston chamber. Preferably, a compression spring is placed between the piston head and the connecting block, and the compression spring pushes the connecting block downward to make the plug block the drip port.

Preferably, an annular spring cavity is placed at the piston head, an upper end of the compression spring goes against a top of the spring cavity, and a lower end of the compression spring goes against a bottom of the piston chamber; a connecting column is placed in the spring cavity, the compression spring is sleeved on an outer side of the connecting column, a liquid guiding hole is placed at a center of the connecting column, an upper end of the liquid guiding hole is in communication with the bottle mouth, the liquid outlet is placed at a lower end of the liquid guiding hole.

Preferably, an internal guiding tube is placed on an outer side of the first connecting tube, an external guiding tube is placed on an outer side of the second connecting tube, and the external guiding tube is slidably sleeved on the internal guiding tube.

Preferably, the lower end of the pressing head contains a connecting hole, the drip port is located at a lower end of the connecting hole, and a diameter of the drip port is smaller than a diameter of the guiding hole; the plug includes an upper apron portion, a lower apron portion and a plug head, an edge of the upper apron portion is slidably sealed with the inner side wall of the second connecting tube, an edge of the lower apron portion is slidably sealed with an inner side wall of the connecting hole, a communication hole is placed between a bottom of the upper apron portion and a top of the lower apron portion; when the plug blocks the drip port, the plug head is in sealing engagement with the drip port.

Preferably, a limiting surface is placed in the second connecting tube, and a top surface of the upper apron portion is opposite to the limiting surface.

Preferably, an outer diameter of the connecting rod is smaller than an inner diameter of the second connecting tube.

Preferably, an annular space is placed between an outer side surface of the piston head and the inner side wall of the first connecting tube, when the piston head inserts into the piston chamber, a side wall of the piston chamber inserts into the annular space.

Preferably, the first connecting tube is fixedly connected with the connecting cover, and the second connecting tube is fixedly connected with the pressing head.

As described above, the present disclosure relates to a drip device, which has the following beneficial effects: since the bottle mouth of the drip bottle is facing downward, the liquid in the drip bottle is charged into the first connecting tube, the infusion channel, the piston chamber, and the infusion channel when the pressing head is not pushed upward, the plug blocks the drip port, and the liquid cannot flow out from the drip port. When the pressing head is pushed upward to move the pressing head upward relative to the connecting cover, the piston head inserts into the piston chamber to separate the infusion channel from the piston chamber, the pressing head continues to move upward, the volume of the piston chamber is compressed, the liquid in the piston chamber will flow back to the drip bottle through the liquid outlet, and the volume of the infusion channel is also compressed, so the liquid pressure in the infusion channel will increase and the connecting rod will be lifted up, thereby causing the plug to move upward to open the drip port, the pressing head continues to move upward, and the liquid in the infusion channel is squeezed out.

After the pressing head is released, the connecting block returns to the initial position, and the plug at the lower end of the connecting rod blocks the drip port again. During the process that the plug moves upward to open the drip port, the liquid is dripped, and the plug moves downward and then blocks the drip port, there is always liquid filling between the plug and the drip port, and the outside air or foreign matter cannot enter the drip device through the drip port. Therefore, the drip device of the present disclosure can reduce the risk of external foreign matter contaminating the liquid agent.

DESCRIPTION OF REFERENCE NUMERALS

1 Drip bottle
2 Bottle mouth
3 Connecting cover
4 First connecting tube
5 Pressing head
6 Drip port
7 Second connecting tube
8 Piston head
9 Connecting rod
10 Connecting block
11 Piston chamber
12 Plug
13 Infusion channel
14 Liquid outlet
15 Compression spring
16 Spring cavity
17 Connecting column
18 Liquid guiding hole
19 Internal guiding tube
20 External guiding tube
21 Connecting hole
22 Upper apron portion
23 Lower apron portion
24 Plug head
25 Communication hole
26 Limiting surface
27 Annular space
28 Socket tube

DETAILED DESCRIPTION OF THE PREFERRED EMBODIMENTS

The embodiments of the present disclosure will be described below. Those skilled can easily understand other advantages and effects of the present disclosure according to contents disclosed by the specification.

It should be understood that the structures, proportions, sizes, and the like, which are illustrated in the drawings of the present specification, are only used to clarify the contents disclosed in the specification for understanding and reading by those skilled, and are not intended to limit the implementation of the present disclosure, thus are not technically meaningful. Any modification of the structure, change of the scale, or adjustment of the size should still fall within the scope of the technical contents disclosed by the present disclosure without affecting the effects and achievable objectives of the present disclosure.

In the meantime, the terms "upper", "lower", "left", "right", "intermediate" and "one" as used in this specification are also for convenience of description, and are not intended to limit the scope of the present disclosure, and the change or adjustment of the relative relationship is considered to be within the scope of the present disclosure without substantial changes in technology.

Figure 1:
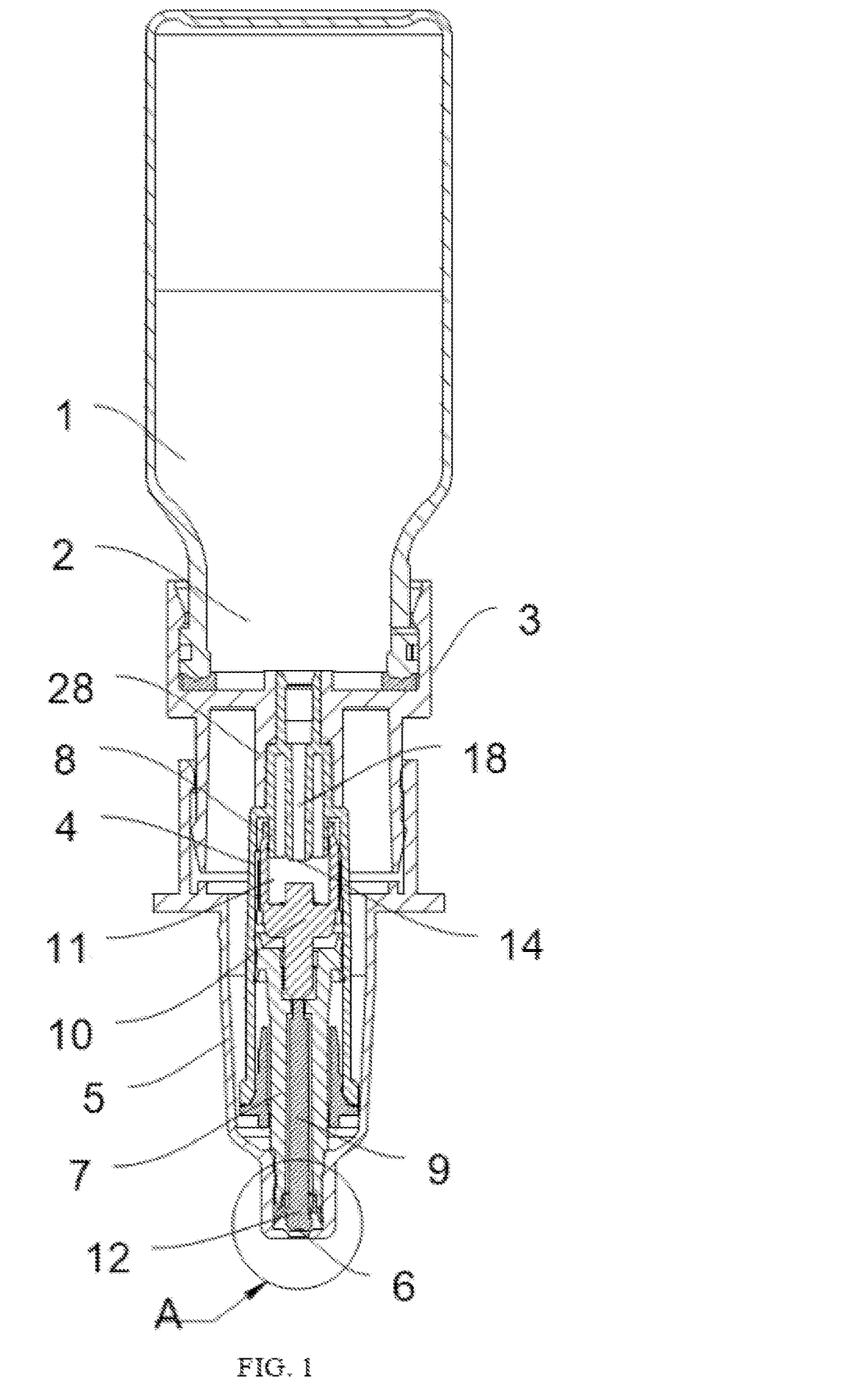
FIG. 1 is a cross-sectional structural view of a drip device of the present disclosure.
Figure 2:
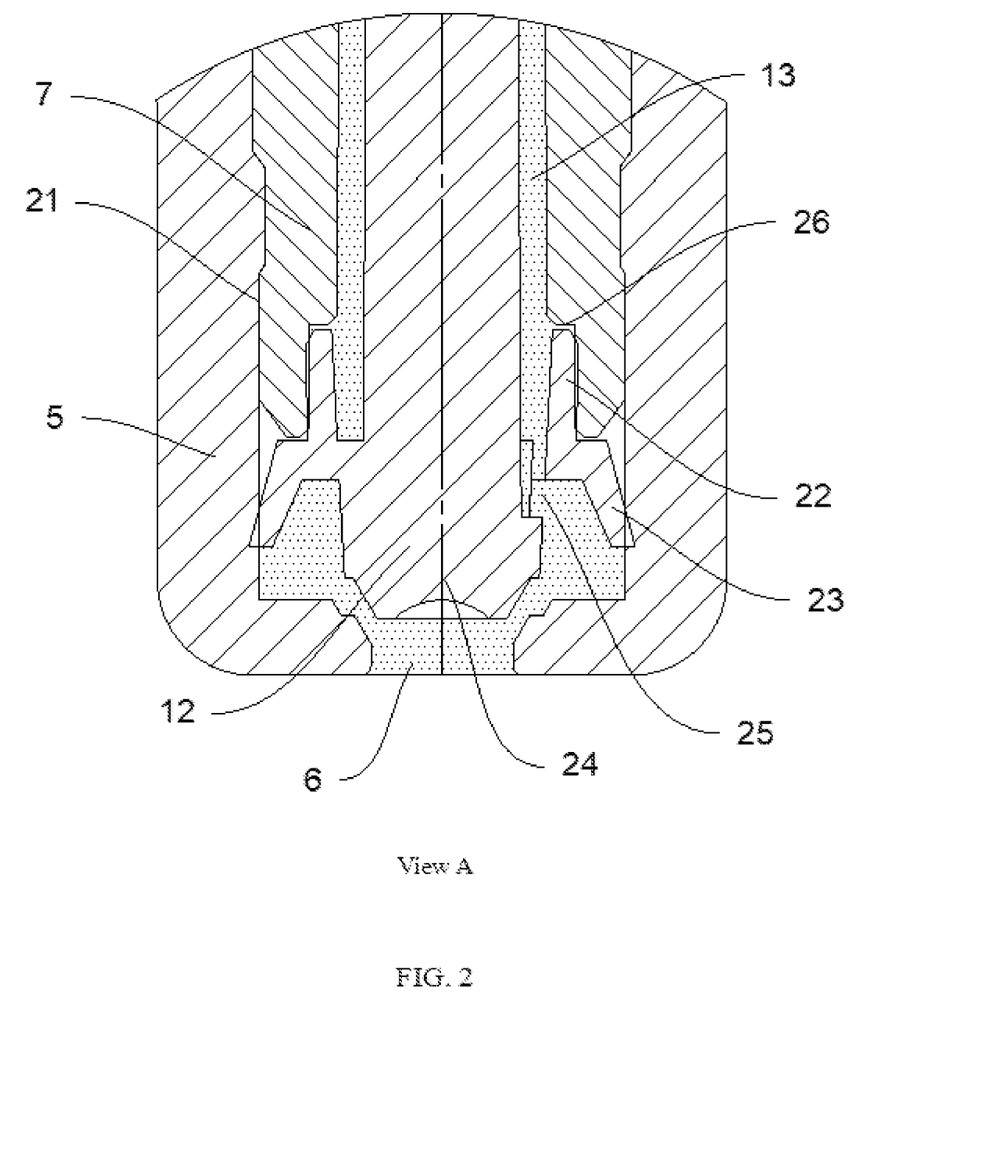
FIG. 2 is an enlarged view of A in FIG. 1.

As shown in FIGS. 1-2, the present disclosure provides a drip device, including: a drip bottle 1 having a bottle mouth 2 facing downward, the bottle mouth 2 is connected with a connecting cover 3, a lower end of the connecting cover 3 is connected with a pressing head 5, the pressing head 5 is reciprocally movable up and down with respect to the connecting cover 3. A first connecting tube 4 extending downward is placed at the lower end of the connecting cover 3, a drip port 6 is placed at a lower end of the pressing head 5, a second connecting tube 7 is placed upward from the drip port 6, an upper end of the second connecting tube 7 extends into the first connecting tube 4 and is slidably sealed with an inner side wall of the first connecting tube 4.

A piston head 8 extending downward is placed in the first connecting tube 4, a connecting rod 9 is placed in the second connecting tube 7, a connecting block 10 is placed at an upper end of the connecting rod 9, the connecting block 10 contains a piston chamber 11 having an opening facing upward, a plug 12 is placed at a lower end of the connecting rod 9, and the plug 12 blocks the drip port 6. An infusion channel 13 is formed by the inner side wall of the first connecting tube 4, an inner side wall of the second connecting tube 7, an outer side wall of the piston head 8, an outer side wall of the connecting block 10, and an outer side wall of the connecting rod 9.

A liquid outlet 14 communicating with the bottle mouth 2 is placed at a lower end of the piston head 8, the infusion channel 13 communicates with the liquid outlet 14 through the piston chamber 11. When the pressing head 5 moves upward relative to the connecting cover 3, the piston head 8 inserts into the piston chamber 11 to separate the infusion channel 13 from the piston chamber 11, thereby increasing the fluid pressure in the infusion channel 13. The connecting rod 9 is therefore lifted up, thus the plug 12 is moved upward to open the drip port 6. Since the bottle mouth 2 of the drip bottle 1 faces downward, the liquid in the drip bottle 1 is charged into the first connecting tube 4, the infusion channel 13, the piston chamber 11, and the infusion channel 13 when the pressing head 5 is not pushed upward, the plug 12 blocks the drip port 6, and the liquid cannot flow out from the drip port 6.

When the pressing head 5 is pushed upward to move the pressing head 5 upward relative to the connecting cover 3, the piston head 8 inserts into the piston chamber 11 to separate the infusion channel 13 from the piston chamber 11. The pressing head 5 continues to move upward, the volume of the piston chamber 11 is compressed, the liquid in the piston chamber 11 will flow back to the drip bottle 1 through the liquid outlet 14. The volume of the infusion channel 13 is also compressed, so the liquid pressure in the infusion channel 13 will increase and the connecting rod 9 will be lifted up, thereby causing the plug 12 to move upward to open the drip port 6. The pressing head 5 continues to move upward, the liquid in the infusion channel 13 is squeezed out.

After the pressing head 5 is released, the connecting block 10 returns to the initial position, and the plug 12 at the lower end of the connecting rod 9 blocks the drip port 6 again. During the process that the plug 12 moves upward to open the drip port 6, the liquid is dripped, and the plug 12 moves downward and then blocks the drip port 6, liquid is always filled between the plug 12 and the drip port 6, the outside air or foreign matter cannot enter the drip device through the drip port 6. Therefore, the drip device of the present disclosure can reduce the risk of external foreign matter contaminating the liquid agent.

Figure 8:
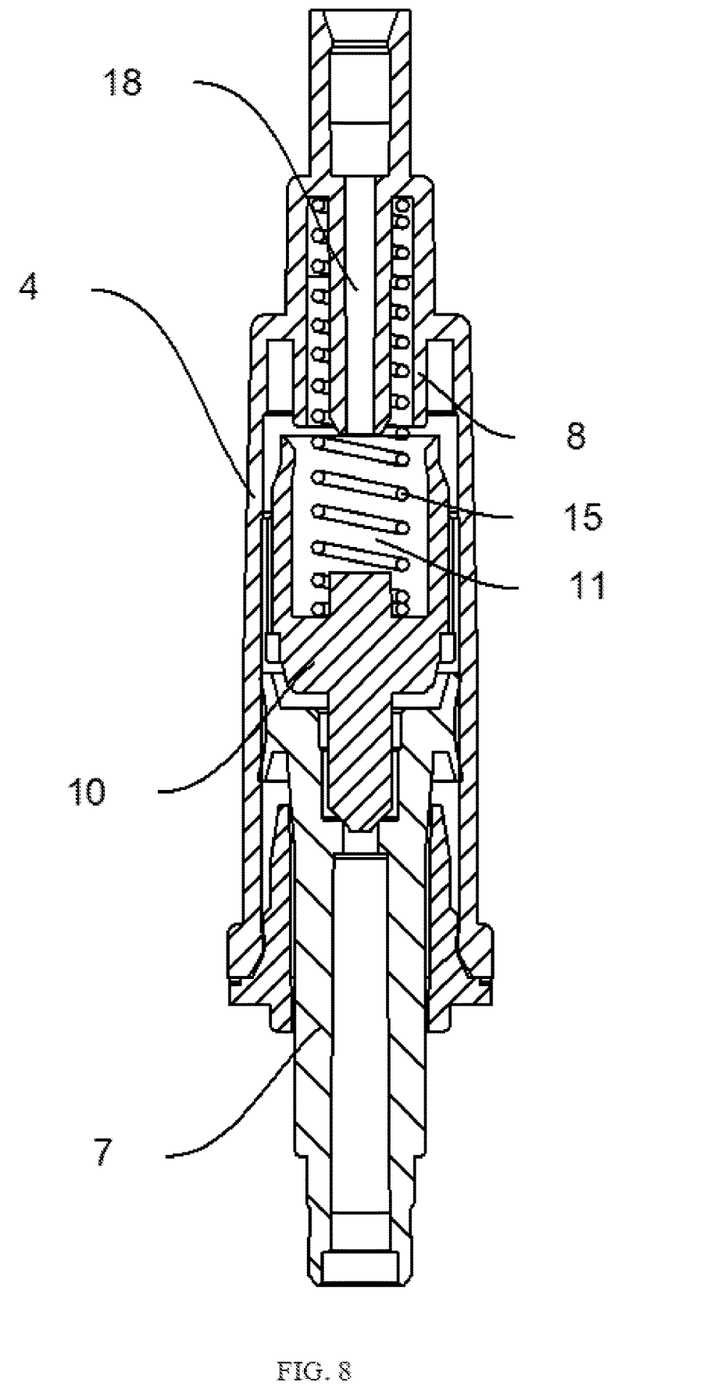
FIG. 8 is a schematic cross-sectional structural diagram of the dispensing pump.

The drip device of the present disclosure uses a dispensing pump to extrude the liquid in the drip bottle 1 from the drip port 6. The structure of the dispensing pump is as shown in FIG. 8 The dispensing pump includes a first connecting tube 4 and a second connecting tube 7, the upper end of the second connecting tube 7 extends into the first connecting tube 4 and is slidingly sealed with the inner side wall of the first connecting tube 4. A liquid guiding hole 18 is placed at the center of the piston head 8. A connecting block 10 is placed at the upper end of the second connecting tube 7, the outer side wall of the connecting block 10 is cylindrical and coaxial with the second connecting tube 7, the connecting block 10 is located at the a cavity between the first connecting tube 4 and the second connecting tube 7. A gap is placed between the outer side wall of the connecting block 10 and the inner wall of the cavity, a piston chamber 11 opposite to the piston head 8 is placed at the connecting block 10.

Referring to FIG. 1, FIG. 3, FIG. 6 and FIG. 8, the drip device of the present disclosure may be assembled by assembling the connecting cover 3, the dispensing pump, the pressing head 5 and the connecting rod 9. The dispensing pump is mounted between the connecting cover 3 and the pressing head 5. A socket tube 28 is placed at the connecting cover 3 The upper end of the first connecting tube 4 inserts into the socket tube 28, the lower end of the second connecting tube 7 also inserts into the connecting hole 21 on the pressing head 5. A connecting rod 9 is placed in the second connecting tube 7, the upper end of the connecting rod 9 is connected with the connecting block 10, and the lower end of the connecting rod 9 is connected with the plug 12.

In the drip device of the present disclosure, the liquid in the drip bottle 1 is dripped through the infusion channel 13. Referring to FIGS. 1-6. When the drip bottle 1 does not drip the liquid, the plug 12 blocks the drip port 6, the infusion channel 13 and the piston chamber 11 are filled with liquid. When the connecting cover 3 moves upward relative to the pressing head 5, the space of the infusion channel 13 is compressed, and a part of the liquid is dripped through the infusion channel 13. When the pressing head 5 is released, the pressing head 5 moves downward, the space of the infusion channel 13 increases and returns to the initial state. When the pressing head 5 continues to move downward to pull the piston head 8 out of the piston chamber 11, the liquid in the drip bottle 1 flows into the infusion channel 13 through the piston chamber 11, and the connecting rod 9 drives the plug 12 to close the drip port 6. Since the liquid in the drip bottle 1 is reduced, the pressure in the inner cavity of the drip bottle 1 is reduced, and the inner cavity of the drip bottle 1 has a certain degree of vacuum with respect to the outside air. Although the pressure in the inner cavity of the drip bottle 1 is lower than the outside air pressure, since the plug 12 has blocked the drip port 6, the air and foreign matter in the outside cannot enter the drip device from the drip port 6.

Figure 3:
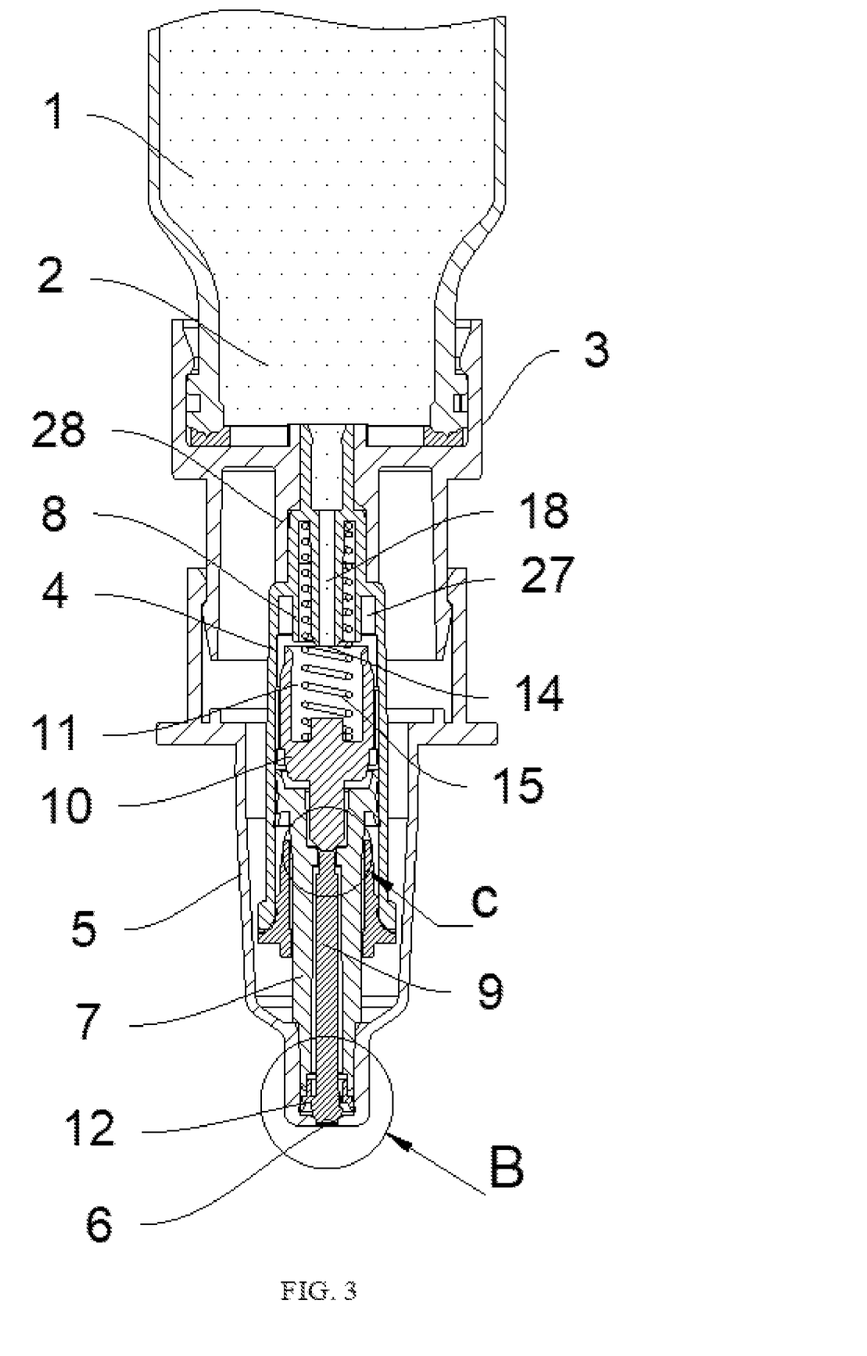
FIG. 3 is a cross-sectional view of a preferred embodiment of the drip device of the present disclosure.
Figure 4:
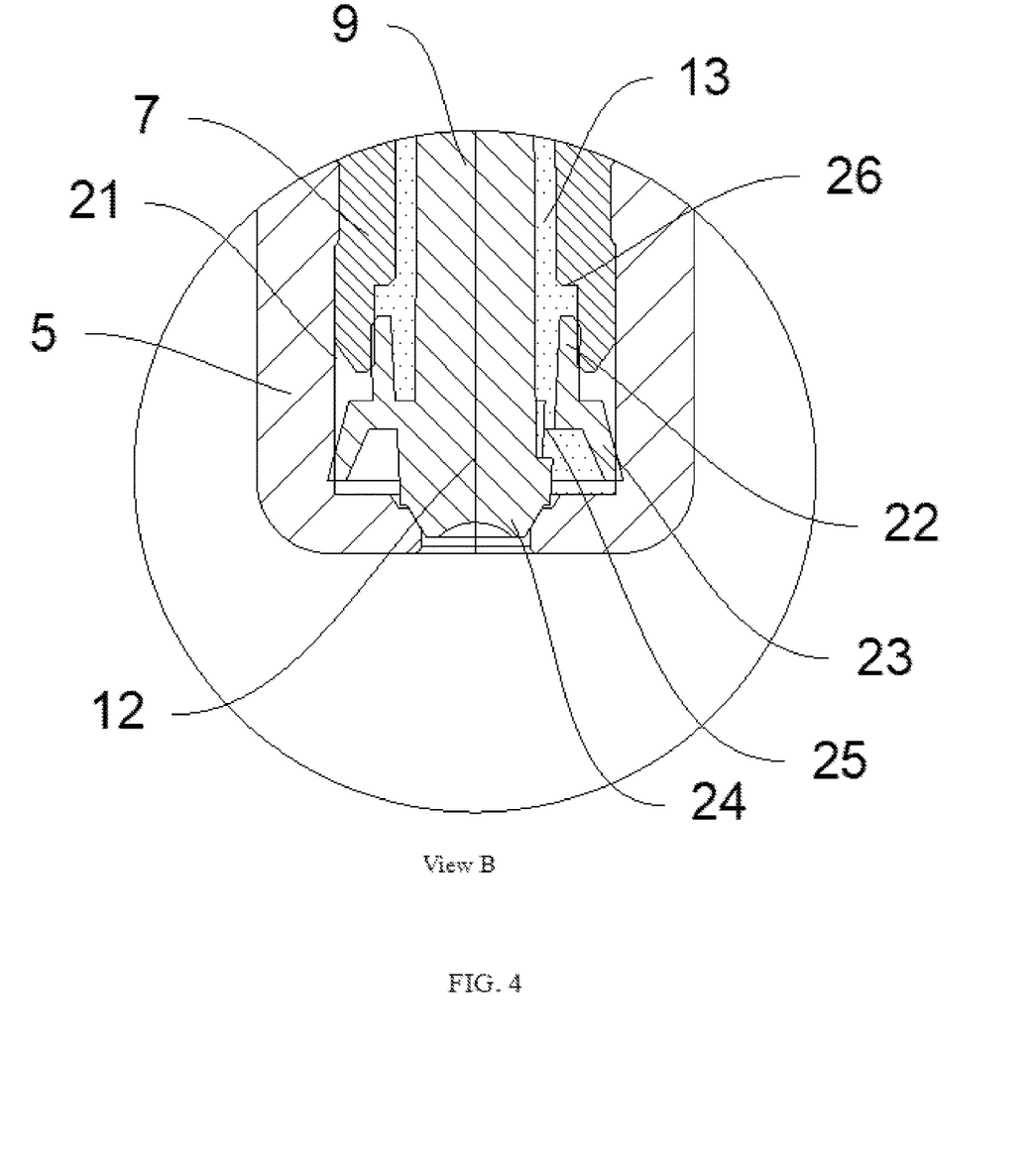
FIG. 4 is an enlarged view of B in FIG. 3.
Figure 5:
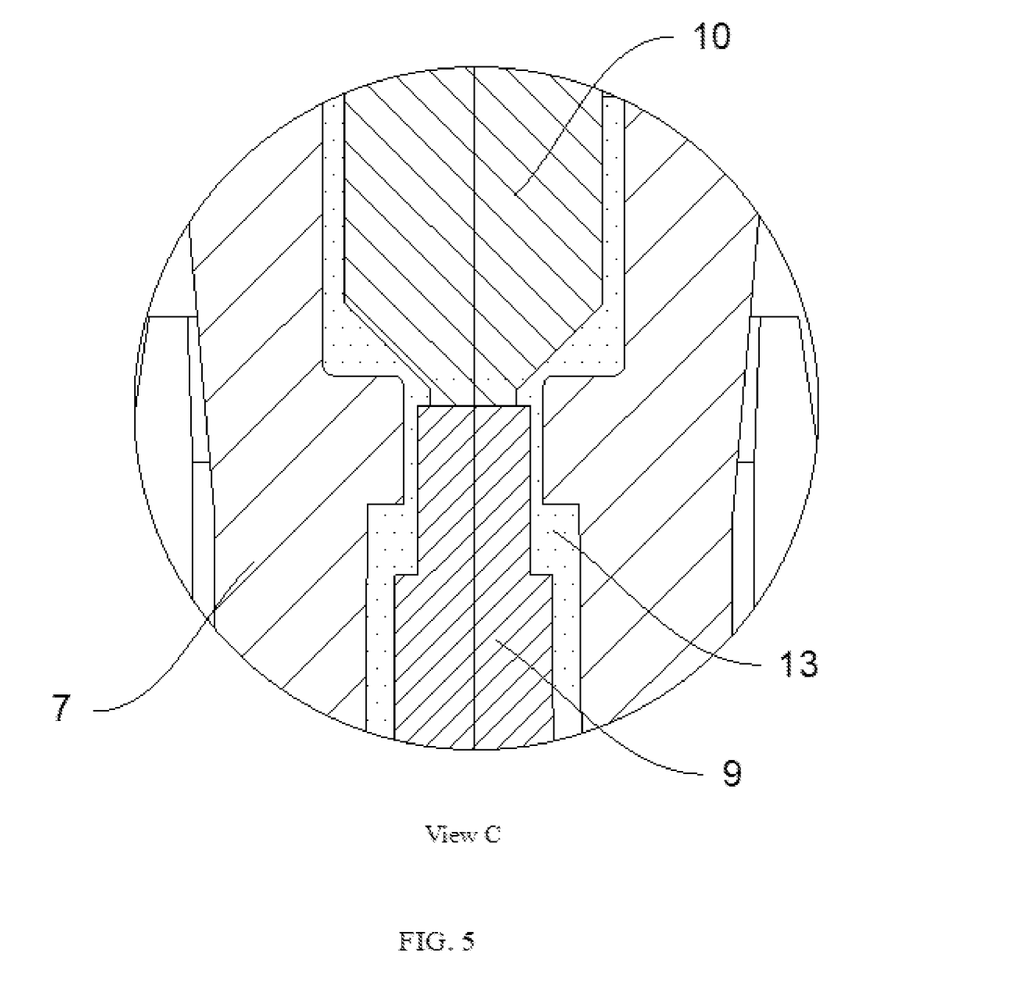
FIG. 5 is an enlarged view of C in FIG. 3.

FIGS. 3-5 show a schematic cross-sectional structural diagram of a preferred embodiment of the drip device of the present disclosure. With respect to the drip device shown in FIGS. 1-2, in the drip device shown in FIGS. 3-5, a compression spring 15 is placed between the piston head 8 and the connecting block 10. When the pressing head 5 is not pressed, the compression spring 15 pushes the connecting block 10 downward to make the plug 12 block the drip port 6, so that when the liquid is not required to be dripped, the compression spring 15 can reliably press the plug 12 on the drip port 6 and seal the drip port 6. After the liquid is dripped, the compression spring 15 can push the connecting block 10 downward to make the piston chamber 11 communicate with the infusion channel 13, and move the connecting rod 9 together with the connecting block 10 to make the plug 12 block the drip port 6 in time.

Figure 6:
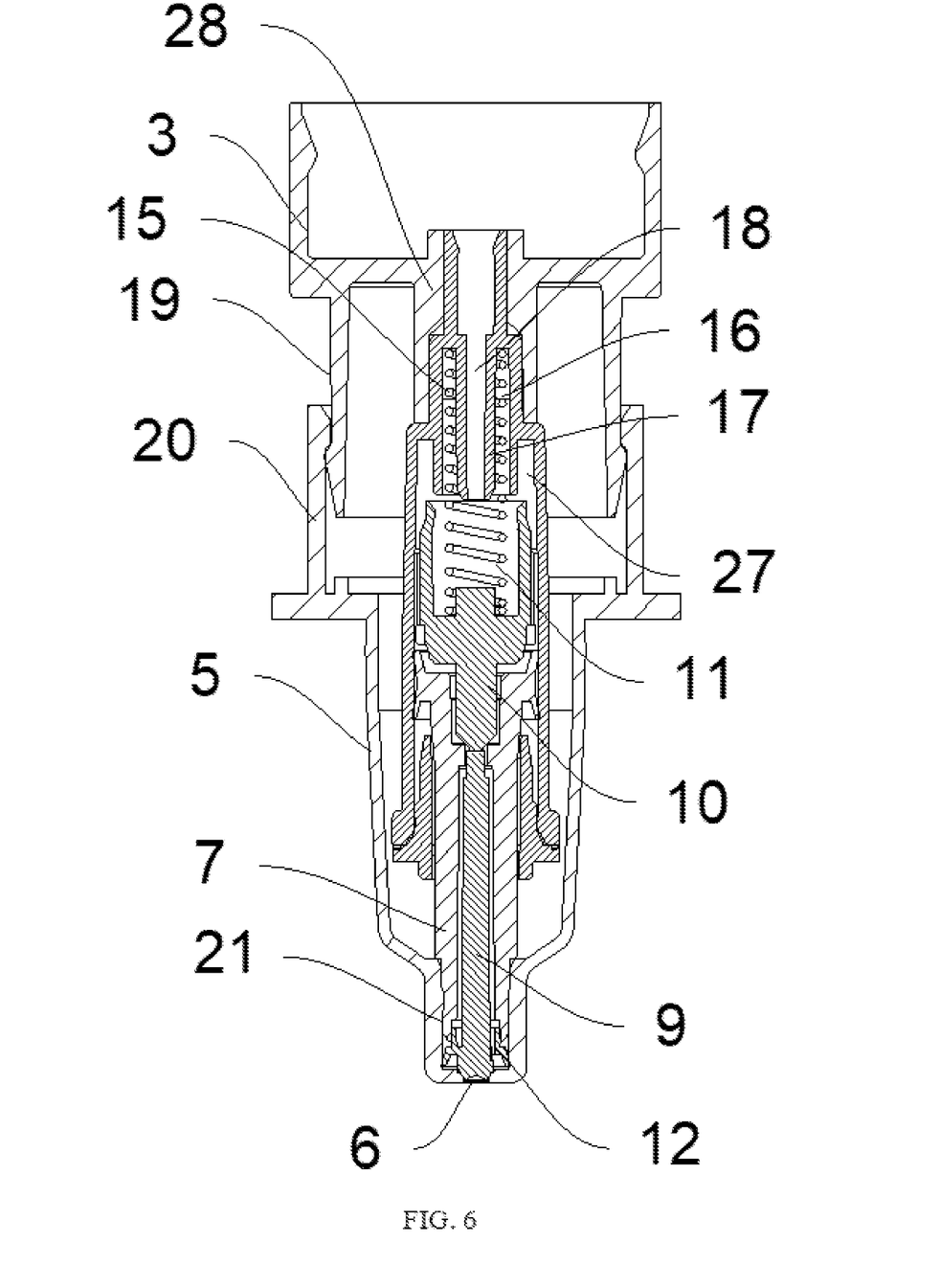
FIG. 6 is a schematic diagram of a connecting structure of a connecting cover, a dispensing pump and a pressing head.

Referring to FIG. 6, as a preferred embodiment, an annular spring cavity 16 is placed at the piston head 8, an upper end of the compression spring 15 goes against a top of the spring cavity 16, and a lower end of the compression spring 15 goes against a bottom of the piston chamber 11. a connecting column 17 is placed in the spring cavity, the compression spring 15 is sleeved on an outer side of the connecting column 17, such that the compression spring 15 does not destabilize during deformation. A liquid guiding hole 18 is placed at the center of the connecting column 17, an upper end of the liquid guiding hole 18 is in communication with the bottle mouth 2, and the liquid outlet 14 is placed at a lower end of the liquid guiding hole 18.

As shown in FIG. 6, an annular space 27 is placed between the outer side surface of the piston head 8 and the inner side wall of the first connecting tube 4, the annular 27 is in communication with the infusion channel 13. When the piston head 8 inserts into the piston chamber 11, the side wall of the piston chamber 11 inserts into the annular space 27, the annular space 27 is compressed to increase the liquid pressure in the infusion channel 13.

As shown in FIGS. 1, 3 and 6, the piston chamber 11 has an upward opening, the piston chamber 11 has a cylindrical shape, the piston head 8 has a cylindrical shape that can fit with the piston chamber 11. When the piston head 8 inserts into the piston chamber 11, the outer side wall of the piston head 8 is slidably sealed with the inner side wall of the piston chamber 11. When the pressing head 5 is not pressed upward, the liquid in the drip bottle 1 is charged by gravity from the liquid outlet 14 to the piston chamber 11 and the infusion channel 13. When the pressing head 5 is pressed upward, the connecting block 10 moves upward, and the piston head 8 inserts into the piston chamber 11 so that the piston chamber 11 is no longer in communication with the infusion channel 13. The connecting block 10 continues to move upwards, and the liquid in the piston chamber 11 returns to the drip bottle 1 due to squeezing, but the pressure of the liquid in the infusion channel 13 increases due to squeezing, therefore the liquid in the infusion channel 13 can only lift up the plug 12 and overflow from the gap between the plug 12 and the drip port 6.

As a preferred embodiment, the outer side surface of the connecting block 10 has a cylindrical shape, the connecting block 10 is coaxially placed with the connecting rod 9, and the outer diameter of the connecting block 10 is larger than the outer diameter of the connecting rod 9. When the pressing head 5 is pressed upward, the liquid at the top of the connecting block 10 communicates with the drip bottle 1 and can return to the drip bottle 1, therefore the liquid pressure at the top of the connecting block 10 is small. In the mean time, the infusion channel 13 is a closed cavity, the liquid in the infusion channel 13 is squeezed, and the pressure is large and acts on the bottom of the connecting block 10. Therefore, the pressure difference between the bottom and the top of the connecting block 10 can promote the upward movement of the connecting block 10 together with the connecting rod 9, so that the plug 12 is separated from the drip port 6 and the drip port 6 is opened, thus the liquid can drip out.

Preferably, the first connecting tube 4 is fixedly connected with the connecting cover 3, and the second connecting tube 7 is fixedly connected with the pressing head 5. As shown in FIGS. 1-6, preferably, the outer diameter of the connecting rod 9 is smaller than the inner diameter of the second connecting tube 7, the gap between the outer diameter of the connecting rod 9 and the inner diameter of the second connecting tube 7 constitutes a part of the infusion channel 13, and the gap between the connecting block 10 and the first connecting tube 4 also constitutes a part of the infusion channel 13.

Referring to FIG. 2 and FIG. 4, FIG. 2 shows the state that the plug 12 moves upward to make the drip port 6 open. FIG. 4 shows the state that the plug 12 is in sealing contact with the side wall of the drip port 6 to block the drip port 6. As a preferred embodiment, the lower end of the pressing head 5 contains a connecting hole 21, the drip port 6 is located at a lower end of the connecting hole 21, and a diameter of the drip port 6 is smaller than a diameter of the guiding hole. The plug 12 includes an upper apron portion 22, a lower apron portion 23 and a plug head 24, an edge of the upper apron portion 22 is slidably sealed with the inner side wall of the second connecting tube 7, an edge of the lower apron portion 23 is slidably sealed with an inner side wall of the connecting hole 21, a communication hole 25 is placed between a bottom of the upper apron portion 22 and a top of the lower apron portion 23. When the pressing head 5 is not moved upward, as shown in FIG. 4, the plug head 24 is in sealing engagement with the side wall of the drip port 6, the plug 12 blocks the drip port 6, and the liquid fills the infusion channel 13. When the pressing head 5 is moved upward, as shown in FIG. 2, the connecting rod 9 moves upward, a gap is placed between the plug head 24 and the side wall of the drip port 6, and the liquid is dripped from the infusion passage 13.

As shown in FIG. 2 and FIG. 4, preferably, a limiting surface 26 is placed in the second connecting tube 7, the top surface of the upper apron portion 22 is opposite to the limiting surface 26. When the plug 12 moves upward until the top surface of the upper apron portion 22 goes against the limiting surface 26, the plug 12 no longer moves upward, thus the flow rate of the liquid can be controlled, so that the liquid does not drip excessively.

Figure 7:
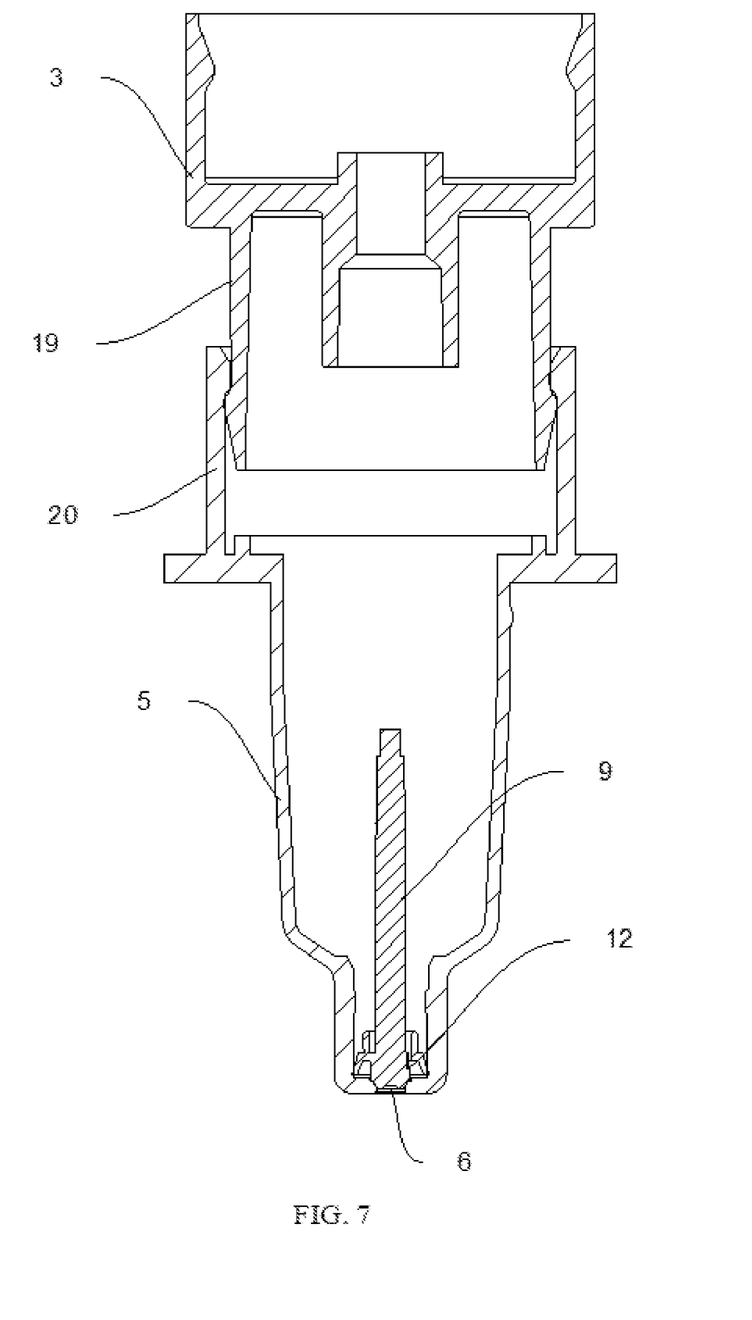
FIG. 7 is a schematic diagram of a connecting structure of a connecting cover, a pressing head and a connecting rod.

As shown in FIGS. 6-7, preferably, an internal guiding tube 19 is placed at the outer side of the first connecting tube 4. An external guiding tube 20 is placed at the outer side of the second connecting tube 7. The external guiding tube 20 is slidably sleeved on the internal guiding tube 19. The first connecting tube 4, the second connecting tube 7, the internal guiding tube 19, the external guiding tube 20, the piston head 8, and the piston chamber 11 are all coaxially arranged, so that the piston head 8 can be sealed with the inner wall of the piston chamber 11 after being inserted into the piston chamber 11.

In summary, the present disclosure effectively overcomes various shortcomings and has high industrial utilization value.

The above-mentioned embodiments are just used for exemplarily describing the principle and effects of the present disclosure instead of limiting the present disclosure. Those skilled in the art can make modifications or changes to the above-mentioned embodiments without going against the spirit and the range of the present disclosure. Therefore, all equivalent modifications or changes made by those who have common knowledge in the art without departing from the spirit and technical concept disclosed by the present disclosure shall be still covered by the claims of the present disclosure.

We claim:

1. A drip device, wherein
the drip device comprises a drip bottle (1) having a bottle mouth (2) facing downward, the bottle mouth (2) is connected with a connecting cover (3), a lower end of the connecting cover (3) is connected with a pressing head (5), and the pressing head (5) is reciprocally movable up and down with respect to the connecting cover (3);
a first connecting, tube (4) extending downward is placed at the lower end of the connecting cover (3), a drip port (6) is placed at a lower end of the pressing head (5), a second connecting tube (7) is placed upward from the drip port (6), and an upper end of the second connecting tube (7) extends into the first connecting tube (4) and is slidably sealed with an inner side wall of the first connecting tube (4);
a piston head (8) extending downward is placed in the first connecting tube (4), a connecting rod (9) is placed in the second connecting tube (7), a connecting block (10) is placed at an upper end of the connecting rod (9), the connecting block (10) contains a piston chamber (11) having an opening facing upward, a plug (12) is placed at a lower end of the connecting rod (9), and the plug (12) blocks the drip port (6), wherein the lower end of the pressing head (5) contains a connecting hole (21), and the drip port (6) is located at a lower end of the connecting hole (21), and the plug (12) includes an upper apron portion (22), a lower apron portion (23) and a plug head (24), wherein an edge of the upper apron portion (221 is slidably sealed with an inner side wall of the second connecting tube (7), an edge of the lower apron portion (23) is slidably sealed with an inner side wall of the connecting hole (21), a communication hole (25) is placed between a bottom of the upper apron portion (22) and a top of the lower apron portion (23), wherein when the plug (12) blocks the drip port (6), the plug head (24) is in sealing engagement with the drip port (6), wherein the upper apron portion (22) extends in an upward direction, and the lower apron portion (23) extends in a downward direction;

an infusion channel (13) is formed by the inner side wall of the first connecting tube (4), the inner side wall of the second connecting tube (7), an outer side wall of the piston head (8). an outer side wall of the connecting block (10), and an outer side wall of the connecting rod (9);

a liquid outlet (14) communicating with the bottle mouth (2) is placed at a lower end of the piston head (8), and the infusion channel (13) communicates with the liquid outlet (14) through the piston chamber (11);

the drip device comprises no spring; and when the pressing head (5) moves upward relative to the connecting cover (3), the piston head (8) inserts into the piston chamber (11) to separate the infusion channel (13) from the piston chamber (11), so that a fluid pressure in the infusion channel (13) increases and the connecting rod (9) is lifted up, thus the plug (12) is moved upward to open the drip port (6).

2. The drip device according to claim 1, wherein when the piston head (8) inserts into the piston chamber (11), the outer side wall of the piston head (8) is slidably sealed with an inner side wall of the piston chamber (11).

3. The drip device according to claim 1, wherein
an internal guiding tube (19) is placed on an outer side of the first connecting tube (4); and
an external guiding tube (20) is placed on an outer side of the second connecting tube (7), and the external guiding tube (20) is slidably sleeved on the internal guiding tube (19).

4. The drip device according to claim 1, wherein
a limiting surface (26) is placed in the second connecting tube (7), and
a top surface of the upper apron portion (22) is opposite to the limiting surface (26).

5. The drip device according to claim 1, wherein an outer diameter of the connecting rod (9) is smaller than an inner diameter of the second connecting tube (7).

6. The drip device according to claim 1, wherein
an annular space (27) is placed between an outer side surface of the piston head (8) and the inner side wall of the first connecting tube (4), and
when the piston head (8) inserts into the piston chamber (11), a side wall of the piston chamber (11) inserts into the annular space (27).

7. The drip device according to claim 1, wherein
the first connecting tube (4) is fixedly connected with the connecting cover (3), and
the second connecting tube (7) is fixedly connected with the pressing head (5).

8. A drip device, wherein
the drip device comprises a drip bottle (1) having a bottle mouth (2) facing downward, the bottle mouth (2) is connected with a connecting cover (3), a lower end of the connecting cover (3) is connected with a pressing head (5), and the pressing head (5) is reciprocally movable up and down with respect to the connecting cover (3);

a first connecting, tube (4) extending downward is placed at the lower end of the connecting cover (3), a drip port (6) is placed at a lower end of the pressing head (5), a second connecting tube (7) is placed upward from the drip port (6), and an upper end of the second connecting tube (7) extends into the first connecting tube (4) and is slidably sealed with an inner side wall of the first connecting tube (4);

a piston head (8) extending downward is placed in the first connecting tube (4), a connecting rod (9) is placed in the second connecting tube (7), a connecting block (10) is placed at an upper end of the connecting rod (9), the connecting block. (10) contains a piston chamber (11) having an opening, facing upward, a plug (12) is placed at a lower end of the connecting rod (9), and the plug (12) blocks the drip port (6), wherein the lower end of the pressing head (5) contains a connecting hole (21), and the drip port (6) is located at a lower end of the connecting hole (21), and the plug (12) includes an upper apron portion (22), a lower apron portion (23) and a plug head (24), wherein an edge of the upper apron portion (22) is slidably sealed with an inner side wall of the second connecting tube (7), an edge of the lower apron portion (23) is slidably sealed with an inner side wall of the connecting hole (21), a communication hole (25) is placed between a bottom of the upper apron portion (22) and a top of the lower apron portion (23), wherein when the plug (12) blocks the drip port (6), the plug head (24) is in sealing engagement with the drip port (6), wherein the upper apron portion (22) extends in an upward direction, and the lower apron portion (23) extends in a downward direction;

an infusion channel (13) is formed by the inner side wall of the first connecting tube (4), the inner side wall of the second connecting tube (7), an outer side wall of the piston head (8), an outer side wall of the connecting block (10), and an outer side wall of the connecting rod (9);

a liquid outlet (14) communicating with the bottle mouth (2) is placed at a lower end of the piston head (8), and the infusion channel (13) communicates with the liquid outlet (14) through the piston chamber (11);

a compression spring (15) is placed between the piston head (8) and the connecting block (10), and the compression spring (15) pushes the connecting block (10) downward to make the plug (12) block the drip port (6); and when the pressing head (5) moves upward relative to the connecting cover (3), the piston head (8) inserts into the piston chamber (11) to separate the infusion channel (13) from the piston chamber (11), so that a fluid pressure in the infusion channel (13) increases and the connecting rod (9) is lifted up, thus the plug (12) is moved upward to open the drip port (6).

9. The drip device according to claim 8, wherein
an annular spring cavity (16) is placed at the piston head (8), an upper end of the compression spring (15) goes against a top of the spring cavity (16), and
a lower end of the compression spring (15) goes against a bottom of the piston chamber (11),
a connecting column (17) is placed in the spring cavity,
the compression spring (15) is sleeved on an outer side of the connecting column (17),
a liquid guiding hole (18) is placed at a center of the connecting column (17),
an upper end of the liquid guiding hole (18) is in communication with the bottle mouth (2), and
the liquid outlet (14) is placed at a lower end of the liquid guiding hole (18).

\* \* \* \* \*